United States Patent
Ben-Haim et al.

(10) Patent No.: US 7,218,963 B2
(45) Date of Patent: *May 15, 2007

(54) FENCING OF CARDIAC MUSCLES

(75) Inventors: Shlomo Ben-Haim, Haifa (IL); Nissim Darvish, Haifa (IL); Yuval Mika, Haifa (IL); Maier Fenster, Petach Tikva (IL)

(73) Assignee: Impulse Dynamics N.V. (AN)

( * ) Notice: Subject to any disclaimer, the term of this patent is extended or adjusted under 35 U.S.C. 154(b) by 348 days.

This patent is subject to a terminal disclaimer.

(21) Appl. No.: 10/188,726

(22) Filed: Jul. 2, 2002

(65) Prior Publication Data

US 2002/0169481 A1    Nov. 14, 2002

(51) Int. Cl.
  *A61N 1/39*    (2006.01)
(52) U.S. Cl. .............................. 607/5; 607/9
(58) Field of Classification Search .............. 607/4, 607/5, 9–11, 25, 66–72, 74
  See application file for complete search history.

(56) References Cited

U.S. PATENT DOCUMENTS

| | | | |
|---|---|---|---|
| 4,554,922 A | 11/1985 | Prystowsky et al. | |
| 5,083,564 A | 1/1992 | Scherlag | |
| 5,205,284 A | 4/1993 | Freeman | |
| 5,800,464 A | 9/1998 | Kieval | |
| 5,814,079 A | 9/1998 | Kieval | |
| 5,871,506 A | 2/1999 | Mower | |

FOREIGN PATENT DOCUMENTS

| | | |
|---|---|---|
| EP | 0727241 | 8/1996 |
| WO | WO 97/25098 | 7/1997 |
| WO | WO 98/10828 | 3/1998 |
| WO | WO 98/10831 | 3/1998 |
| WO | WO 98/10832 | 3/1998 |

OTHER PUBLICATIONS

H. Antoni, et al., Polarization Effects of Sinusoidal 50-Cycle Alternating Current on Membrane Potential of Mammalian Cardiac Fibres, Pflugers Arch. 314 pp. 274-291 (1970).

Bers, "Excitation-Contraction Coupling and Cardiac Contractile Force" Kluwer Academic Publishers, London (1993).

*Primary Examiner*—Jeffrey R. Jastrzab
(74) *Attorney, Agent, or Firm*—Wolf, Block, Schorr & Solis-Cohen LLP; William H. Dippert

(57) ABSTRACT

An apparatus for blocking the electric activity of an area of tissue, comprises circuitry (S) for creating a long non-excitatory electric signal between at least two points (R1, R2) located in the vicinity of a muscle.

66 Claims, 8 Drawing Sheets

FENCING OF CARDIAC MUSCLES

FIELD OF THE INVENTION

The present invention relates to the field of medicine. More particularly, the invention relates to means for reversibly blocking the electric activity of cells. In particular, the invention relates to a method and means for reversibly blocking the muscle activity of various muscles (also referred to hereinafter as "fencing"), including the cardiac muscle.

BACKGROUND OF THE INVENTION

Many activities of the human body involve the contraction of muscles. For instance, movement of the limbs, breathing activity, etc. The most complex and vital muscular activity of the human body is that of the heart, which functions as a pump and which, by contracting at the required times and in the required manner, controls the flow of blood throughout the body.

The heart is composed of different parts, which contract differently and with different timing, in order to permit the aforementioned pumping activity. The contraction of the heart is controlled by electric stimuli, which are generated at the cellular level by chemical reaction. However, it is well known in the art to control such activity, i.e., the timing of the contraction of the cardiac muscle, by the action of externally applied electric stimuli, through the so-called "pace maker".

In a copending PCT patent application No. PCT/IL97/00012, filed Jan. 8, 1997, the specification of which is incorporated herein by reference, of which the inventors herein are also inventors, there is described a method and apparatus for modifying the force contraction of at least a portion of a heart chamber, which comprises applying a non-excitatory electric field, for a predetermined period of time, at a delay after activation.

In the aforesaid PCT patent application No. PCT/IL97/00012 and in another copending PCT/IL patent application of the same applicants herein, filed on the same day as the present application, entitled "Apparatus and Method for Controlling the Contractility of Muscles", and identified as the specification of which is incorporated herein by reference, there is described a method and apparatus for decreasing the force contraction of at least a portion of a heart chamber, which comprises applying a non-excitatory electric field, for a predetermined period of time, at a delay after activation. The ability to reduce the contractility is of importance in a variety of situations, e.g., during surgery or as an aid in healing of hibernated areas of a heart after myocardial infarct.

The mechanical activity of excitable cells is directly connected to their electric activity. This is most evident in the activity of the heart, which has a relatively complex electric functioning which is responsible for pacing, contraction of various areas of the cardiac muscle, as well as to the organized consecutive or simultaneous contraction of various zones. Any disturbance in the electric function of the cells may severely affect, or even stop mechanical activities of the cell. Conduction problems are also related to a variety of congenital and acquired diseases. A detailed discussion of such phenomena can be found, e.g., in the book by Donald M. Bers, "Excitation-Contraction Coupling and Cardiac Contractile Force", Kluwer Academic Publishers, Dordrecut, Boston, London, 1993.

Treatment of electrical cellular malfunctioning is mainly confined to systemic treatment, such as by drugs or, in some cases with heart diseases, a pace maker may be required. Localized treatment, such as local ablation, is also sometime attempted. However, there are several conditions that cannot be treated by localized treatment, unless the activity of the relevant muscle is totally blocked for a suitable period of time, in a reversible manner. One example of such a condition is ventricular fibrillation or ventricular tachycardia arrhythmias, which can be induced by abnormal activity localized in a susceptible area.

Another important tool in heart therapy is the use of defibrillators. Defibrillation is a process in which an electronic device helps reestablish normal contraction rhythms in a heart that is not functioning properly, by delivering an electric shock to the heart. Defibrillators can be external or internal (implanted or inserted). Typically, a defibrillator is designed to automatically detect episodes of bradycardia, ventricular tachycardia (VT), fast ventricular tachycardia (FVT), and ventricular fibrillation (VF). When an arrhythmia is detected, the device will deliver the programmed pacing, cardioversion or defibrillation therapy. The device typically has two electrodes which are implanted. The defibrillator, as said, stops arrhythmia by delivering an electric shock, which is a painful and harmful treatment, particularly if repeated often and, importantly, it is not a localized treatment, but rather it is applied to the whole cardiac muscle.

It has now been surprisingly found, and this is an object of the present invention, that it is possible to block the activity of a localized area of cells, such as a muscle (i.e., to carry out a "fencing"), in a reversible manner, and thus to block the cell's activity for a desired period of time.

It is an object of the invention to provide apparatus for carrying out the fencing of a desired tissue area having electric activity and thereby temporarily and reversibly blocking the activity of said area.

It is another object of the invention to provide a method for treating a patient suffering from a condition treatable by temporarily blocking the electric activity of a tissue.

It is yet another object of the invention to provide a method and apparatus useful in therapy, which can be exploited in treating a variety of conditions, such as epilepsy, arrhythmia, stooping ticks, and shockless defibrillation.

Other objects and advantages of the invention will become apparent as the description proceeds.

SUMMARY OF THE INVENTION

In one aspect, the invention relates to apparatus for blocking the electric activity of an area of a tissue comprising circuitry for creating a long non-excitatory electric potential (LNT) between at least two points located in the vicinity of a muscle.

According to a preferred embodiment of the invention, the apparatus comprises circuitry for controlling the start time of the electric potential generated between said at least two points. According to another preferred embodiment of the invention, the apparatus comprises circuitry for controlling the duration of the electric potential generated between said at least two points. According to still another preferred embodiment of the invention, the apparatus comprises circuitry for controlling the magnitude of the electric potential generated between said at least two points.

The apparatus of the invention is particularly useful when the tissue on which it is employed is a cardiac muscle.

According to a preferred embodiment of the invention, the circuitry for creating a long non-excitatory electric potential between said at least two points comprises one or more electrode, e.g., carbon electrodes.

According to another preferred embodiment of the invention, the apparatus comprises circuitry for causing a long non-excitatory electric current to flow between at least two points located in the vicinity of a muscle.

The apparatus of the invention is useful, inter alia, for performing heart surgery, and comprises circuitry for creating a long non-excitatory electric potential between at least two points located in the vicinity of the cardiac muscle. According to another preferred embodiment of the invention, the apparatus comprises circuitry for causing a long non-excitatory electric current to flow between at least two points located in the vicinity of the cardiac muscle.

Illustrative examples of heart surgery in which the device of the invention can be utilized are a bypass operation and other minimal invasive cardiac operation.

The invention is further directed to a method for blocking the mechanical and/or electric activity of an area of a tissue, comprising creating a long non-excitatory electric potential between at least two points located in the vicinity of the tissue, and controlling one or more of the parameters consisting of start time, duration, magnitude and polarity of the long non-excitatory electric potential created between said at least two points. According to a preferred embodiment of the invention, the method for blocking the electric activity of an area of a tissue comprises causing a long non-excitatory electric current to flow between at least two points located in the vicinity of the tissue, and controlling one or more of the parameters consisting of start time, duration, magnitude and polarity of the long non-excitatory electric current flowing between said at least two points.

The invention also encompasses a method for performing heart surgery, comprising blocking the mechanical and/or electric activity of a treated area of the cardiac muscle, by creating a long non-excitatory electric signal between at least two points located in the vicinity of the muscle, and controlling one or more of the parameters consisting of start time, duration, magnitude and polarity of said long non-excitatory electric signal, thereby to obtain the desired blocking of the mechanical and/or electric activity of the cardiac muscle at the treated heart area and thereafter performing surgery thereon.

In one aspect, the invention is directed to a method for blocking the mechanical and/or electric activity of an area of a tissue, comprising:

providing means for creating an electric potential between at least two points located in the vicinity of said area of the tissue;

providing means for causing a non-excitatory electric current to flow between said at least two point; and controlling the start time, duration and magnitude of the electric current flowing between said at least two points, such that the total duration of the long non-excitatory electric signal exceeds the threshold value at which the activity of the tissue is blocked.

In another aspect the invention is directed to a method of treating a condition induced by electric activity of cells, comprising treating a patient in need thereof with the application of a long non-excitatory signal between at least two points located in the vicinity of the affected cells, such that the total duration of the long non-excitatory electric signal exceeds the threshold value at which the electric activity of the tissue is blocked.

According to a preferred embodiment of the invention, the apparatus comprises the means for controlling the start time, duration and magnitude of the electric current flowing between said at least two points located in the vicinity of an area of the tissue comprise pulse generating means for generating a plurality of pulses, with a given frequency, and wherein the timing of said pulses is adapted to the activity of the tissue, the total duration of said series of pulses constituting the duration of the long non-excitatory signal.

The invention is also directed to defibrillating apparatus comprising circuitry for creating a long non-excitatory electric potential between at least two points located in the vicinity of a muscle, and to a method for carrying out a defibrillation in a patient in need thereof, comprising blocking the electric activity of an area of a tissue, comprising creating a long non-excitatory electric potential between at least two points located in the vicinity of the tissue, and controlling one or more of the parameters consisting of start time, duration, magnitude and polarity of the long non-excitatory electric potential created between said at least two points until defibrillation is achieved. According to a preferred embodiment of the invention, the method comprises causing a long non-excitatory electric current to flow between at least two points located in the vicinity of the tissue, and controlling one or more of the parameters consisting of start time, duration, magnitude and polarity of the long non-excitatory electric current flowing between said at least two points until defibrillation is achieved.

As will be apparent to the skilled person, the LNT-signal must be timed so as to have a delay relative to the activity of the muscle. If this is not taken into account a deleterious effect may result. For instance, when the cardiac muscle is treated, fibrillation may be induced by an electric signal which is not properly timed. Additionally, the LNT-signal will typically be composed of a plurality of short peaks, applied at a given frequency, and the total length of time during which said short peaks are applied constitutes the total duration of the LNT-signal. In order to deal with the above needs, in a preferred embodiment of the invention the means for controlling the start time, duration and magnitude of the electric current flowing between said at least two points located in the vicinity of an area of the tissue, comprise pulse generating means for generating a plurality of pulses, with a given frequency, and wherein the timing of said pulses is adapted to the activity of the tissue, the total duration of said series of pulses constituting the duration of the long non-excitatory signal.

According to a preferred embodiment of the invention there is provided a defibrillating apparatus for the localized and selective defibrillation at one or more locations of a heart, comprising for each of said one or more locations:

a) sensing means for sensing a change in electric activity of the heart or of a portion thereof;

b) analyzing circuitry, for analyzing said change in electric activity;

c) logic circuitry, for deciding on the appropriate therapy to be delivered to the sensed area or to the area of the heart which is responsible for the change in electric activity, said appropriate therapy comprising the application to the affected area of a long non-excitatory signal of a suitable magnitude, start time, duration and frequency;

d) signal delivery means, for delivering said long non-excitatory signal to said area of the heart; and e) control means, for controlling the delivery of said long non-excitatory signals to each affected area, and for timing the delivery of different signals to two or more different affected areas of the heart.

The signal delivery means can be of various suitable types and may include, e.g., one or more electrodes.

In the context of the present invention, by "long non-excitatory current", or "long non-excitatory potential", or "long non-excitatory signal", it is meant to indicate a signal which does not cause a propagating action potential in the muscle cells (which may start a new pacing or contraction of the muscle). In other words, the non-excitatory electric stimulation effected by a non-excitatory electric pulse is such that it does not induce propagating activation potentials in the cardiac muscle cells. Rather, such pulses affect the response of the heart muscle to the action potentials, by affecting cell electrical characteristics within selected segments of the cardiac muscle.

As described in the abovementioned PCT patent application PCT/IL97/00012, while a DC current is typically used as the base line for the non-excitatory signal, it is also possible to supply a signal which is a complex signal, for instance, a signal generated by superimposing an AC current on the DC base signal, so as to generate a waveform of varying envelope. Any suitable signal can be superimposed, having any shape, e.g., square wave or sinusoidal wave, as will be apparent to the skilled person. Thus, according to one preferred embodiment of the invention the apparatus further comprises means for superimposing on a DC signal one or more waveforms of given frequency and amplitude, thereby to generate a complex signal.

The apparatus can be provided in various forms, depending on the specific needs. One example of apparatus suitable for carrying out the invention is described in detail and claimed in a copending PCT patent application of the same applicants herein, entitled "Cardiac Output Controller", filed on the same day as the present application and identified as the description of which is incorporated herein by reference. Another example of suitable apparatus, coupled to a pacemaker device, is the subject of another copending PCT patent application of the same applicants herein, entitled "Cardiac Output Enhanced Pacemaker", filed on the same day as the present application and identified as the specification of which is also incorporated herein by reference. However, as said, the invention is not intended to be limited to any particular construction of device used to carry it out.

According to a preferred embodiment of the invention, the apparatus is intended for long term treatment, and is an insertable device. An insertable device is a device which can be introduced for a limited period of time (i.e., up to a few weeks), for a prolonged therapy. It differs from an implanted device inasmuch as it is not meant to be carried by the patient indefinitely or for very long periods of time. According to another preferred embodiment the apparatus can be implantable. According to still another preferred embodiment of the invention, the apparatus, whether intended for short or long term treatment, is an extra corporal device.

As explained above, the means for causing a non-excitatory DC electric current to flow, are preferably synchronized to heart activity. According to a preferred embodiment of the invention, the means for causing a non-excitatory DC electric current to flow operate not at every beat of the heart, e.g., operate every 1, 2 or 3 beats of the heart.

As will be appreciated by the skilled person, the actual set of operating parameters used (current, length of pulse, number of electrodes, lag after pacing signal, etc.), will be dependent on the specific use made of the invention, and the skilled person will easily be able to devise the optimal set of parameters for a given application. Where no pace maker is used, the delay is preferably calculated from the natural activity of the patient's heart, or from the local electrical activity.

The invention can be conveniently carried out using sensing means coupled to control means, which sense the electric activity of the muscle and activate the LNT-signal at the appropriate time.

It should further be noted that, while in the above discussion and in the examples to follow particular emphasis has been put on cardiac muscles, this has been done only for the purpose of illustration, and the invention is by no means meant to be limited in any way to cardiac muscle. On the contrary, the invention is applicable to other tissue which has an activity which is dependent on electric signals.

While a variety of electrodes can be used, and the invention is in no way limited to any particular type of electrode, particularly preferred suitable electrodes for this purpose are, e.g., carbon electrodes.

BRIEF DESCRIPTION OF THE DRAWINGS

The above and other characteristics and advantages of the invention will be more readily apparent through the following detailed description of preferred embodiments thereof, with reference to the appended drawings, wherein.

DEFINITIONS

Figure 1:
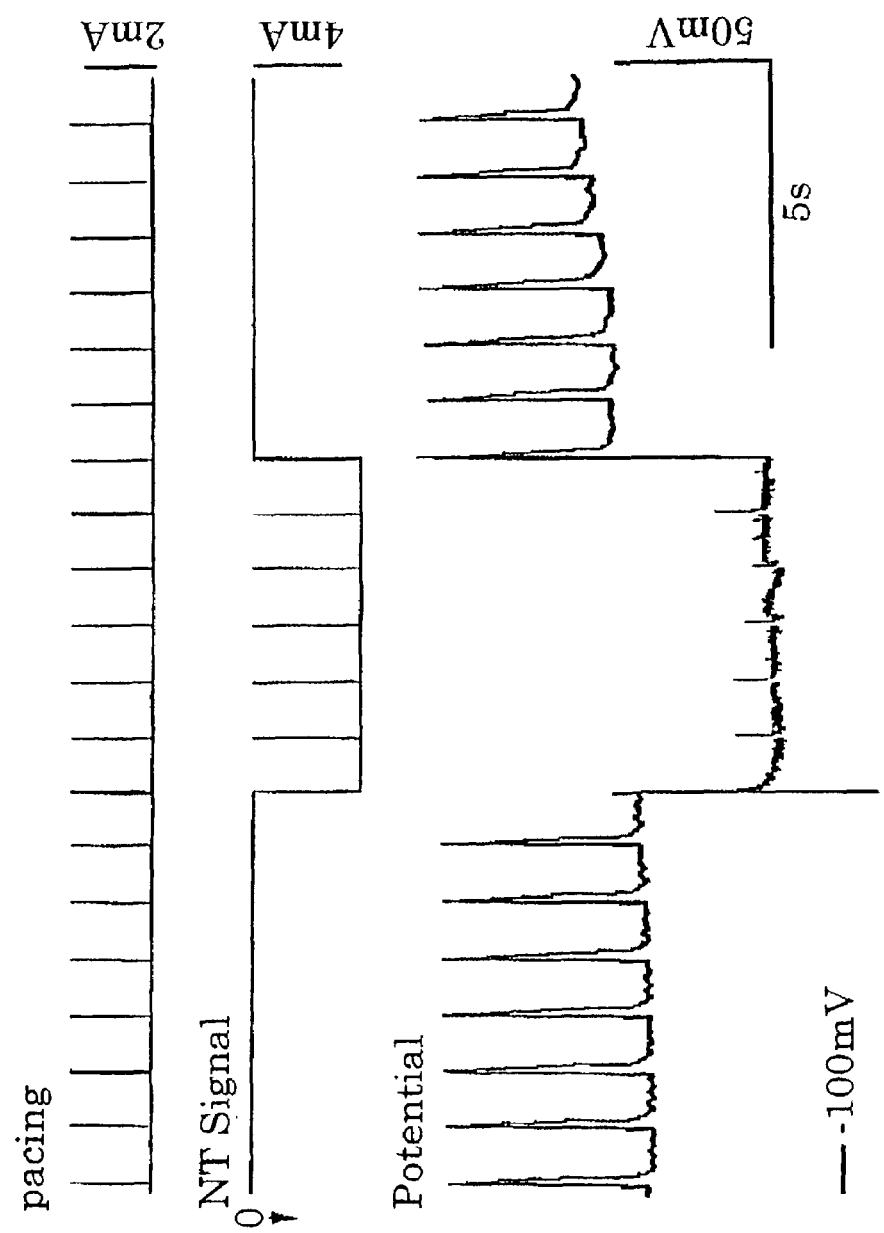
FIGS. 1–7 show the effect of the application of an LNT-signal to a rabbit papillary muscle, under varying conditions.

The following terms and abbreviations, used throughout this specification, are defined below, for the sake of clarity:
I.M.=Intramuscular
IV=Intra Venous
LV=Left Ventricle
RV=Right Ventricle
VF=Ventricular Fibrillation

DETAILED DESCRIPTION OF PREFERRED EMBODIMENTS

The invention will now be illustrated through detailed experiments. Experiments in vitro were carried out using isolated rabbit papillary muscle, and the protocol for its isolation is detailed below.

Equipment

The following equipment which will be referred to hereinafter, is now briefly described for the sake of clarity:

Plugsys system: The plugsys system is an incorporating plug in modules for measuring, controlling and data processing in connection with recorders and computers. In general, it functions as an amplifier which increases the sensitivity of the measuring of biological signals. One such device, used in the experiments described herein, is manufactured by HSE, Germany.

Millar: This device (manufactured by Millar Instruments, USA), is a micro manometers transducer that can be connected to a battery operated bridge (which is the interface box) and the output can be digitized using an A/D converter. In another mode of operation the transducer is connected through a DBA (plugsys DC Bridge Amplifier), which is an amplifier connected to transducers to measure pressure force (manufactured by HSE, Germany).

Isolated Papillary Muscle Protocol

Animals: New Zealand white rabbits (males) from Israel (Yokneam) or an hybrid of New Zealand White and local albino rabbits (males, AniLab, Rehovot) are kept in room temperature, 2–3 per cage (35×55×65 cm), under natural light conditions. Daily feeding of dry food (Rabbit Mix—Code 590), and unlimited water supply. The cages and the room are cleaned daily, Instruments A. for solution making: Scales (by Mettler Toledo, model P8303, Max 310 gram, d=1 mGram) magnetic stirrer. by Freed electric. Weights 10 Kg (d=50 gram) by Moznei Shekel, Gas tanks with mixed 95% $O_2$+5% $CO_2$" pressure regulators, pH meter by Mettler Toledo, model 320 PH, ice machine 45 Labotal.

Dissection chamber (HSE, Hugo Sachs Elektronik, Germany), Steered organ bath type 813 (I-18E) including temperature controller type 319, Force Transducer type F30 with amplifier type 660 and calibration unit (HSE), Stereoscope (Olympus, Japan), Digital micro manipulator (HSE), Manipulator, Anti-vibration table (TMC, USA), Faraday cage, Fiber optic illuminator (HSE), Current and Voltage clamp amplifier (axon Instruments, USA), stimulators (grass instruments, USA), Micro-pipette puller model pp-83 (Narishige, Japan) Current source ISO 10 and ISO-50 (home made) supplying 10 and 50 mA correspondingly and Oscilloscope, 20 MHz (Gould, England), Computers: PowerPC 9500/I50, (Apple, USA), or Pentium, 166 MHz, Data Acquisition Boards: PCI-MIO-16XE50, 16 bite, or the PCI-M10-16E-2, 12 bite board by National Instrument, software: LabView for windows, by National Instrument (USA). Data acquisition and analysis program are home made, The program includes data acquisition and on-line analysis, programmable experiment execution, programmable signal output. The off-line analysis program analyze different parameters of muscle twitch and action potentials.

Solution

The Krebs-Heseleit Solution (KHS) was prepared using materials from Sigma (Israel): 0.32 g/lit KCl (4.5 mM), 6.99 g/lit NaCl (118.0 mM), 2.01 g/lit $NaHCO_3$ (24.0 mM), 0.285 g/lit $MgSO_4.7H_2O$ (1.19 mM), 0.16g/lit $KH_2PO_4$ (1.18 mM), 2.0 g/lit Glucose (11.0 mM), and 0.37 g/lit $CaCl_2.2H_2O$ (2.52 mM), added after bubbling with a 95% $O_2$+5% $CO_2$ gas mixture for 20 minutes.

Solution preparation: Distilled water (ion exchange column Zilion, Israel and ultra filtration by EasypurLF, Israel) are used to prepare the KHS stock solution (X 20, 5L). The chemicals except $CaCl_2$ are used. The stock solution is discarded after 1 week of refrigeration, For each day of experiment fresh solution is prepared (5L) out of the stock solution, $CaCl_2$ is added, and the solution is bubbled (95% $O_2$/5% $CO_2$) for 20 min. and titrated to a pH of 7.4. Bubbled KHS at room temperature is used for perfusion of the papillary muscle kept in an organ bath.

Anesthesia and heart dissection: animal is brought from the cage to a scale for measuring body weight, The animal is anesthetized by 1 Vembutal 1–1.2 mg/Kg body weight I.P, using −5 cc syringe and 23 Gage needle. The level of anesthesia is checked by the animal reflex to a pinch. When the animal is deeply anesthetized, the skin over the chest is cut off and the chest wall is cut open exposing the heart. Using scissors and a forceps the pericardium is cut and the heart is dissected out by cutting all the blood vessels. Immediately after cutting, the heart is placed in an ice cold (4° C.) and oxygenated KHS.

Papillary muscle dissection: The heart is transferred to a fresh ice-cold KHS and than to the dissection chamber, containing ice-cold continuously oxygenated KHS. The heart is fixed to a rubber pad with insect pins and than the left ventricle is opened exposing the papillary muscles. A silk (60) thread is tied around the tendon of the papillary muscle and the muscle is dissected out using fine twizers. The dissected muscle (length of 2–3 mm) is transferred to the organ bath and the heart is kept at 4° C. for further dissections of the other papillary muscles.

The Steiert Organ Bath: The muscle is placed in an organ bath, and than fixed to the chamber by a plastic holder. The silk thread tied to the tendon is hooked to a rigid hook on the force transducer (on the opposite side) to give isometric conditions. The papillary muscle is continuously perfused (7–12 ml/min,) with oxygenated KHS kept at a regulated temperature of 37° C.

Pacing and Stimulation

Pacing stimuli (typically 1 Hz, 2 ms duration, and amplitude of 2 mA) are given by two Ag-AgCl electrodes which are part of the organ bath and are placed under the muscle. The electrodes are covered with AgCl layer, chlorodizing by 5 mA, 5 ms pulses during perfusion. Constant current stimuli (CCU) are given to the upper part of the muscle using graphite electrodes (diameter of 0.5 mm fitted to a glass pipette) placed 2–3 mm apart along the fibers' line (contraction axis). The muscle length is adjusted to maximal isometric force and left for equilibration period of 30 min.

EXAMPLE 1

Temporary and Reversible Electrical Block

A rabbit papillary muscle was paced using a pacing signal of 2 mS duration at 1 Hz, and 3 mA amplitude (twice the threshold measured for that muscle). An LNT-signal was applied 1 mS delay after the pacing signal, having a duration of 998 mS and an amplitude of 5 mA. The resulting effect is shown in FIG. 1.

It can be seen from FIG. 1 that the electrical muscle activity was totally blocked by the LNT signal from responding to the pacing signal, and thus contraction of the muscle was inhibited. Total recovery of the muscle electrical activities seen after the end of the application of the LNT signal.

EXAMPLE 2

Mechanical Block

A rabbit papillary muscle was paced using a pacing signal of 2 mS duration at 1 Hz, and 2.2 mA amplitude, and an LNT-signal was applied 400 mS after the pacing signal, with duration of 200 mS and amplitude of 0.5 mA. The polarity of the LNT-signal was inverted during the experiment (polarity direction in the figures is arbitrary, since there is no absolute "+" and "−" signs for the LNT signal, and the suitable polarity is established for each specific case).

Figure 2:
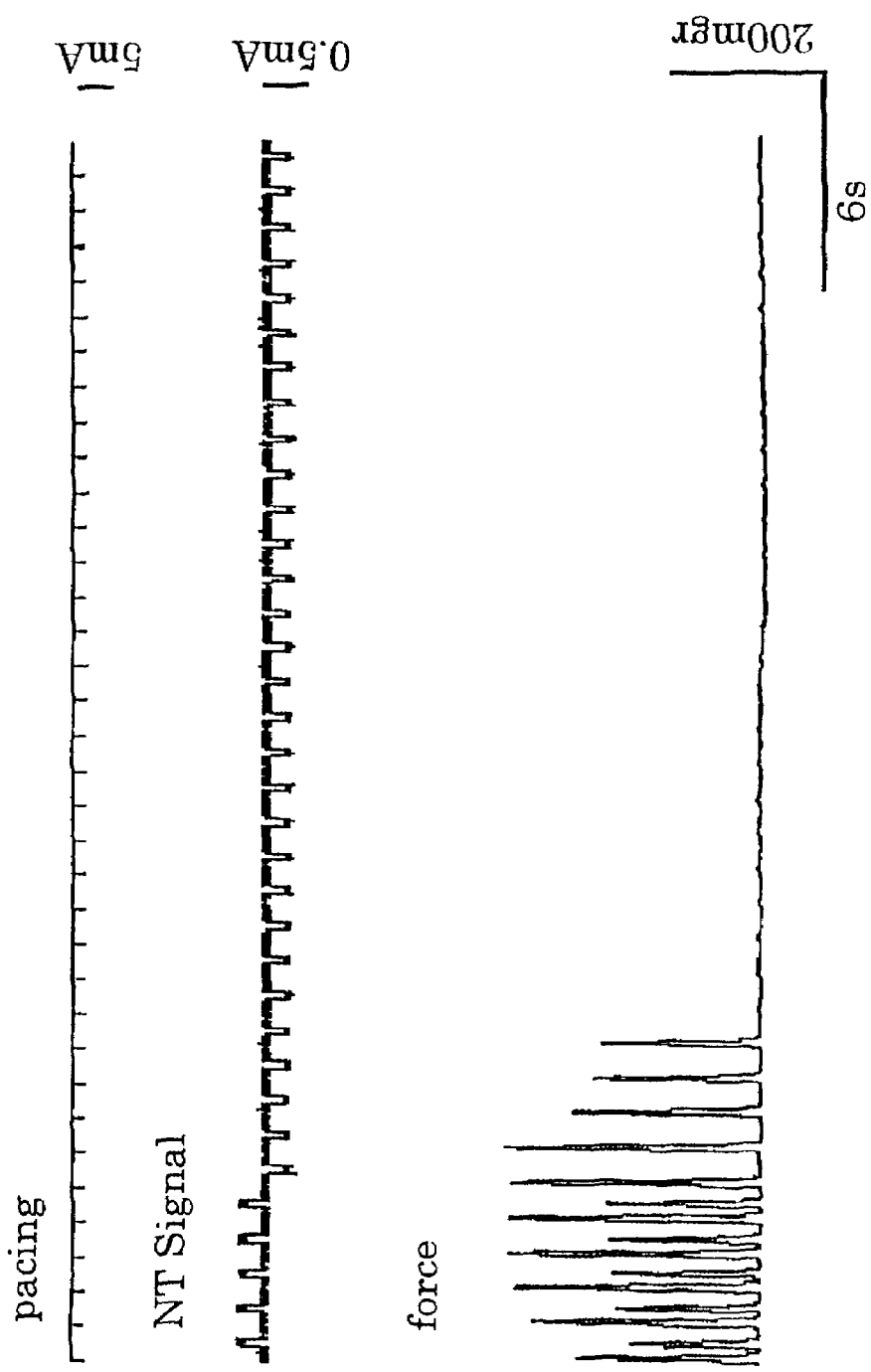

As seen in FIG. 2, the initial inverse signal is an excitatory signal, and as such it causes corresponding contractions in the muscle, indicated by the intervening peaks between the response to the pacing signal, and no blocking of the contraction muscle activity occurs. When the polarity is switched, however, to be as in FIG. 1, blocking of the muscle activity is achieved.

EXAMPLE 3

A rabbit papillary muscle was paced using a pacing signal of 2 mS duration at 1 Hz, and 3 mA amplitude. The above pacing parameters are twice of the relative threshold values needed for evoking a contraction in this muscle. An LNT-signal was applied after 1 mS of the pacing signal, having a duration of 998 mS and an amplitude of 15 mA. The resulting effect is shown in FIG. 3.

Figure 3:
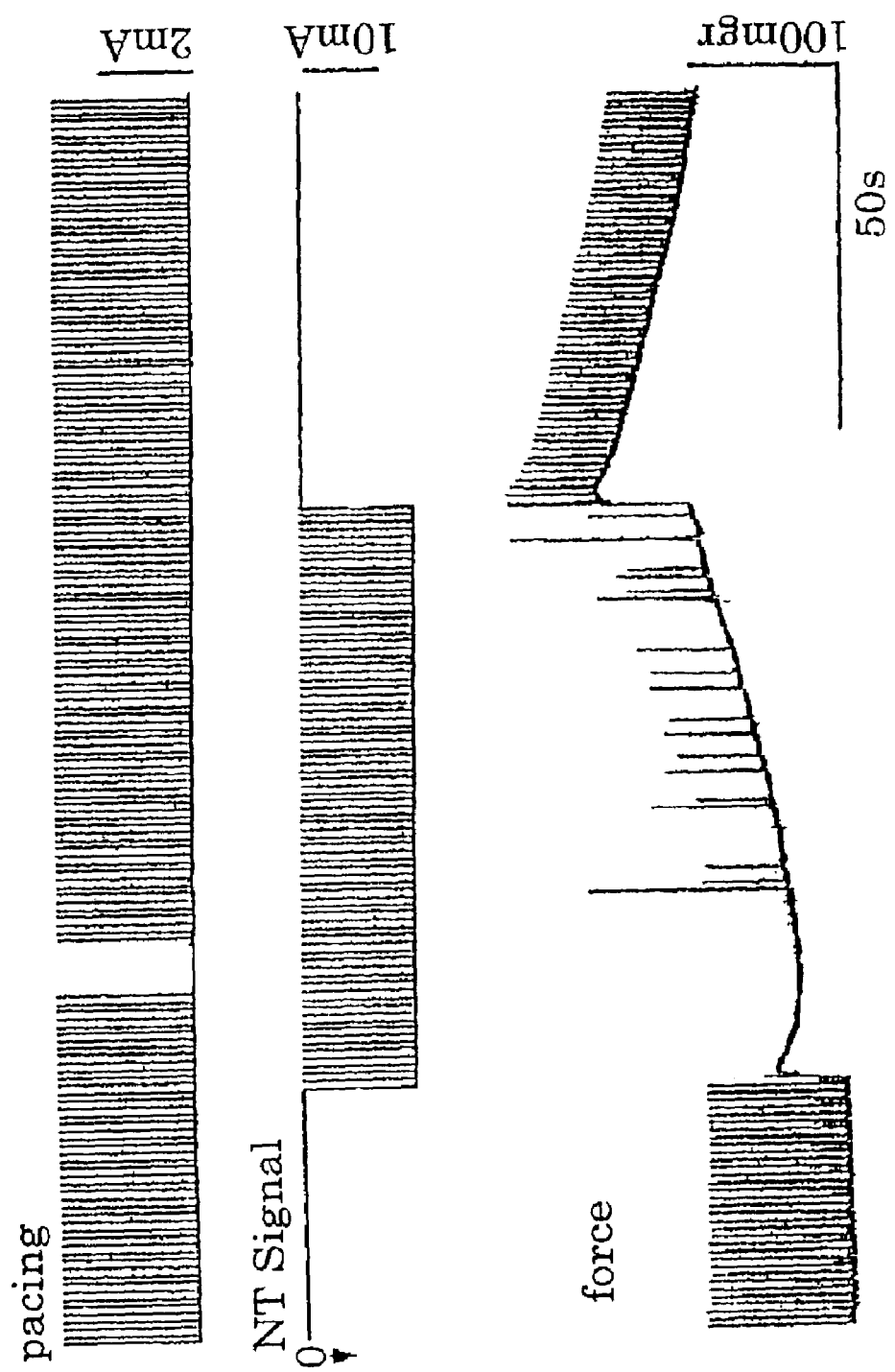

As is seen in FIG. 3, total block of the muscle activity was initially obtained, followed by a casual escape from that block, which was not repeatable and which appears to be due to an occasional experimental problem. As is seen in the figure, stopping the pacing signal did not result in contractions, even though the LNT-signal employed was 5 times greater in amplitude than the pacing signal. This result, again, indicates that the LNT-signal is a non-excitatory signal in its nature, and that activity of the muscle was completely blocked. Upon termination of the LNT-signal the muscle returned to normal rhythm contraction. A residual effect on muscle contraction can be seen on the muscle during recovery, for several minutes.

EXAMPLE 4

Figure 4:
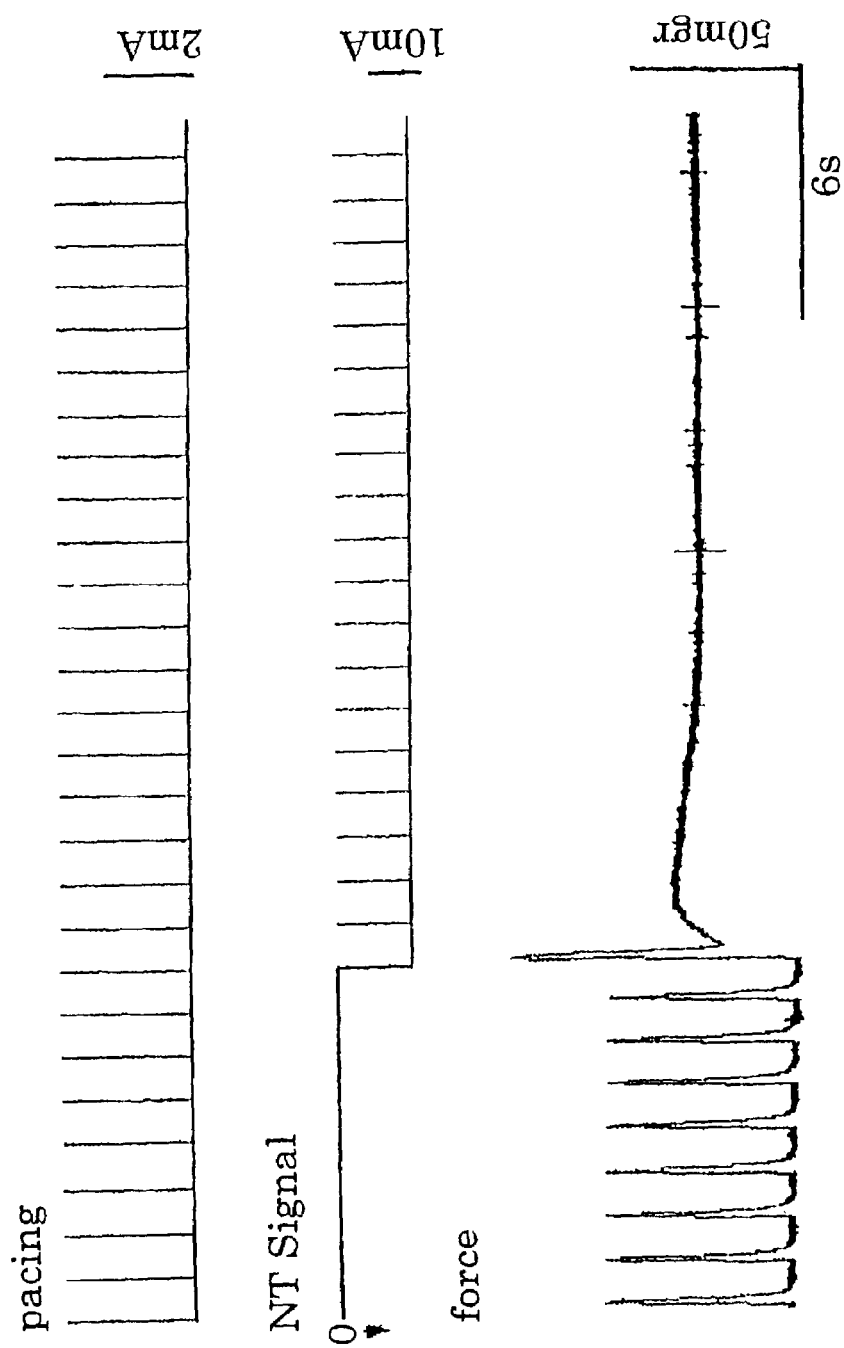

A rabbit papillary muscle was paced using a pacing signal of 2 mS duration at 1 Hz, and 3 mA amplitude. The above pacing parameters are twice the relative threshold values for the muscle employed. An LNT-signal was applied after 1 mS of the pacing signal, having a duration of 998 mS and an amplitude of 15 mA. The resulting effect is shown in FIG. 4.

The muscle activity was totally blocked.

EXAMPLE 5

Rabbit papillary muscle was paced with the following parameters: Pacing: 0.5 Hz, 2 mS duration, 3.5 mA; and LNT-Signal was applied at 1 mS delay, 1999 mS duration, 15 mA, 0.5 Hz.

Figure 5:
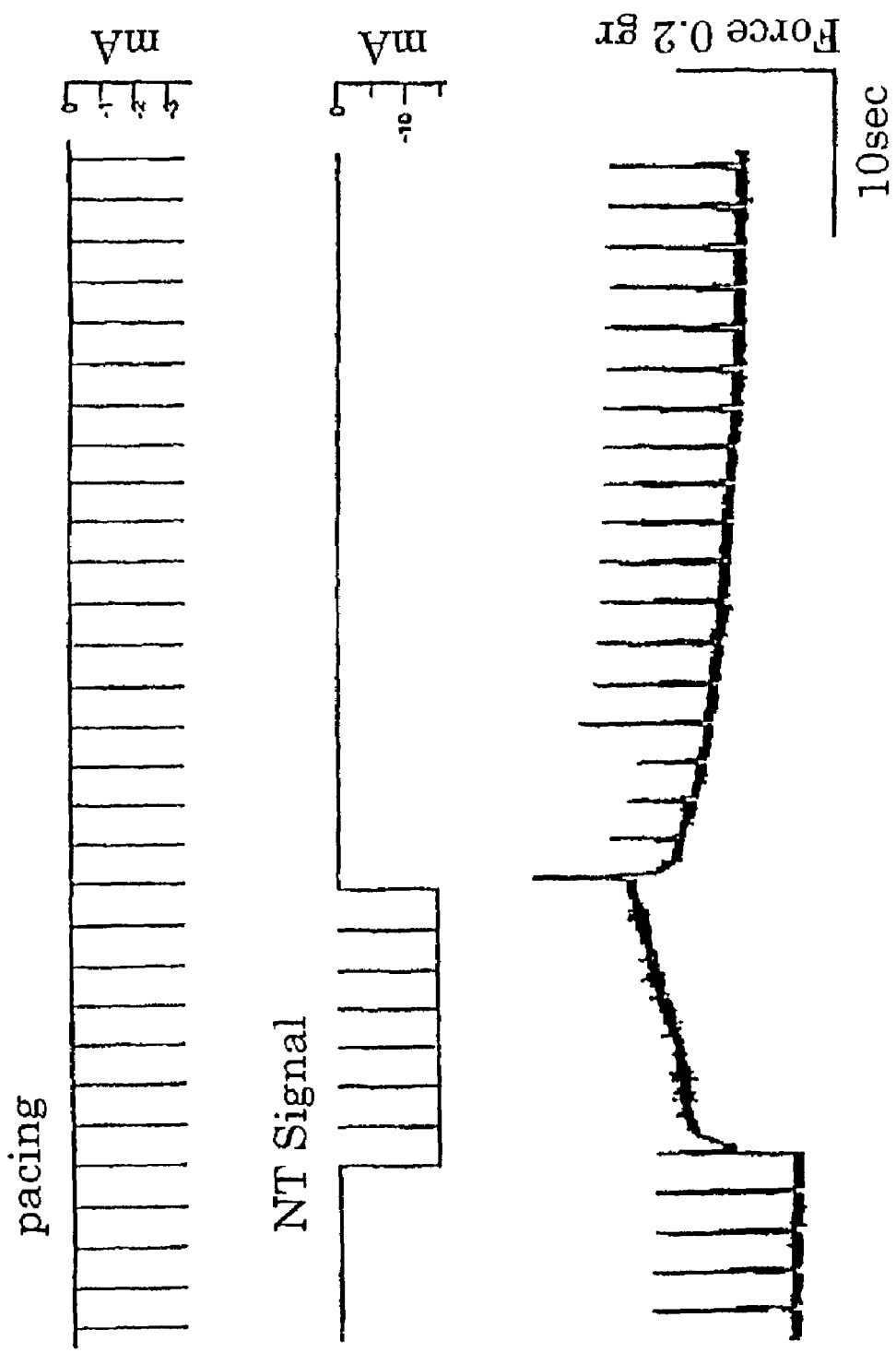

The results show a complete blocking of muscle activity (FIG. 5), and gradual recovery of the muscle is observed after turning off the LNT signal.

EXAMPLE 6

Example 1 was repeated, using the following parameters: Pacing: 1 Hz. 2 mS duration, 3 mA (these parameters are twice the threshold measured for this muscle); LNT-Signal: 1 mS delay, 998 mS duration, 5 mA, 1 Hz.

Figure 6:
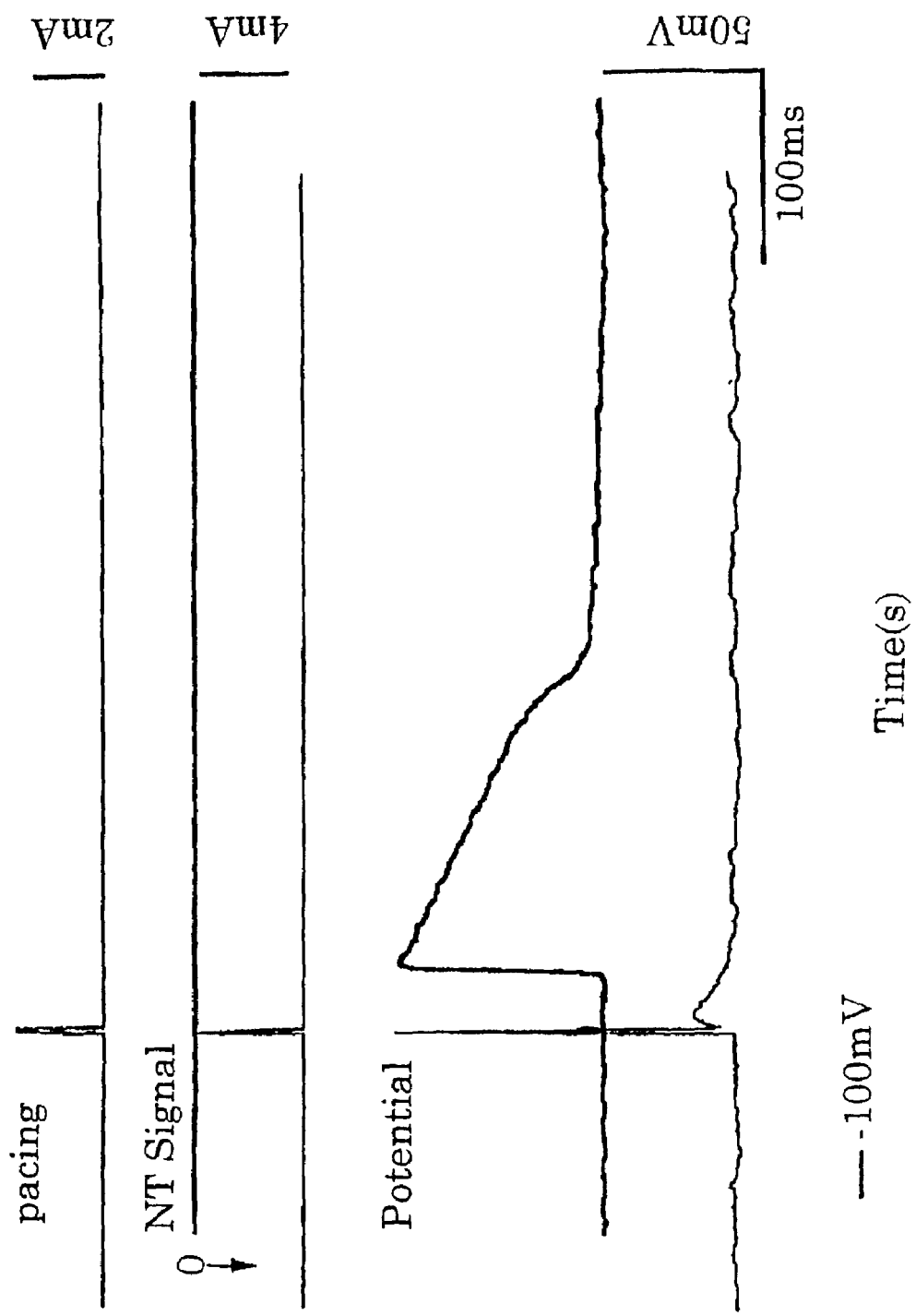

A blow-up of one action potential resulting from a pacing signal superimposed on the potential measured when both pacing and LNT signals were applied is shown in FIG. 6. Application of the LNT-signal resulted in a total block of cell action potential, measured by an intercellular electrode (thin line in the figure).

Thick line: action potential as a result of pacing signal only. Thin line: superimposing of the changes in membrane potential during LNT-signal application, showing that a cell failed to respond by a new action potential to the pacing signal.

This experiment shows that the LNT-signal blocked all muscle activity.

EXAMPLE 7

Example 1 was repeated, using the following parameters: Pacing: 1 Hz, 2 mS duration, 3 mA (these parameters are twice the threshold measured for this muscle); LNT-Signal: 1 mS delay, 998 mS duration, 15 mA, 1 Hz.

Figure 7:
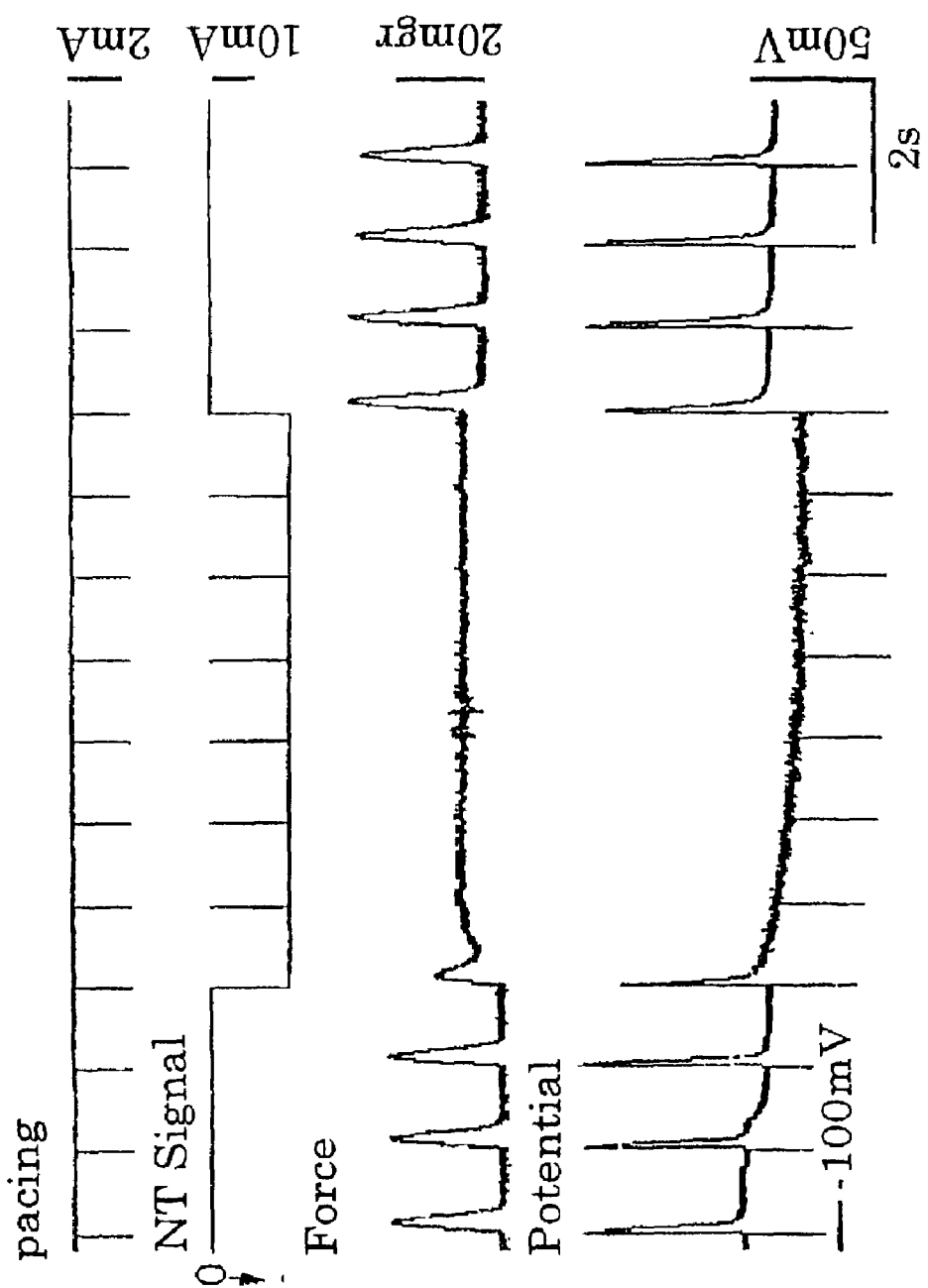

The results are shown in FIG. 7. Application of the LNT-signal (downward deflection) resulted in a total block of muscle electrical activity, measured by an intercellular electrode, and of the contraction activity of the muscle. At the end of the NT-signal the potential and the contraction force undergo full recovery. This result shows that the LNT-signal blocked all mechanical and electrical activity.

Figure 8:
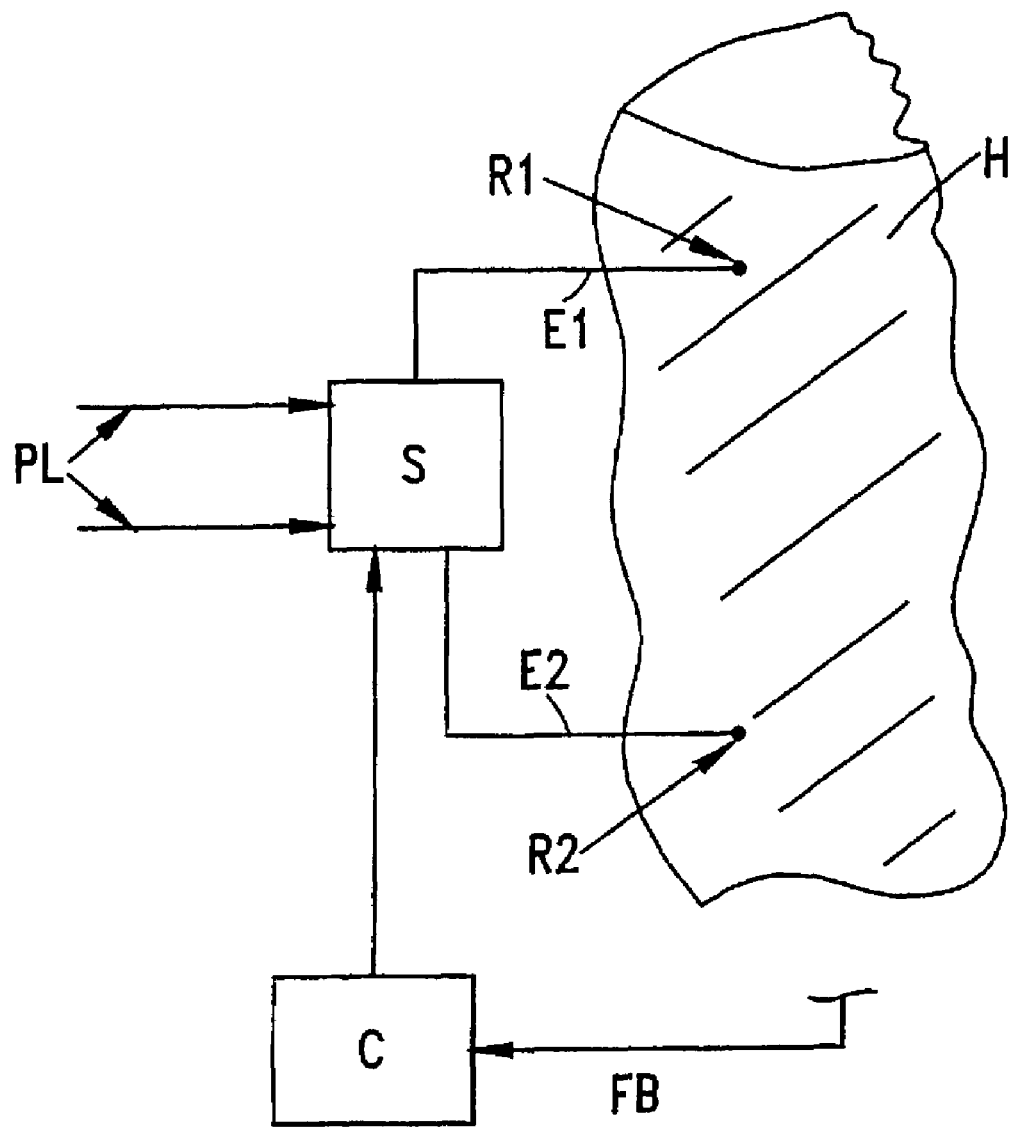
FIG. 8 is a schematic representation of an apparatus according to one embodiment of the invention.

Referring now to FIG. 8, a schematic representation of an apparatus according to one embodiment of the invention is seen. In this scheme, a portion of a cardiac muscle, H, is brought into closed positioned relationship with two electrodes, E1 and E2, the ends of which are positioned at root position R1 and R2, respectively. The electrodes receive the voltage and/or current from a signal generator S, the construction of which is conventional and well know to skilled persons, and which is therefore not described here in detail, which in turn receives power from a power line, PL, connected to an autonomous power source or to the mains, as the case may be. Illustrative examples of suitable apparatus may be found, e.g., in the aforesaid copending PCT/IL patent applications entitled "Cardiac Output Controller" and "Cardiac Output Enhanced Pacemaker" both filed on the same day as the present application, the specifications of which are incorporated herein by reference. The activity of the power signal generator S is controlled by a controller, C, which may be a microprocessor, or which may be an external controlling device, e.g., a PC or other computer. The controller C controls the parameters of the signal generated by the signal generator, such as current intensity, frequency and timing, and may use both preset parameters (e.g., the frequency of pulse generation) and feed-back input, e.g., from apparatus which monitors heart or other parameters, or from a pace maker which supplies the pacing signal. These input signals are collectively schematically indicated in the figure as FB. Of course, the apparatus is only schematically shown, for the sake of brevity. And the skilled person will easily be able to devise many different kinds of apparatus suitable to supply the signal needed in carrying out the invention.

All the above description and examples have been given for the purpose of illustration and are not intended to limit the invention in any way. Many modifications can be carried out in the invention: for instance, many different tissues and different conditions can be treated; furthermore, different LNT-signals can be employed, all without exceeding the scope of the invention.

The invention claimed is:

1. Apparatus for blocking the activity of an area of a tissue, said apparatus comprising one or more electrodes capable of being located in the vicinity of said area of a tissue and circuitry for creating long non-excitatory electric pulses and applying said pulses to said electrodes, thereby generating a long non-excitatory potential between at least two points located in the vicinity of said area of a tissue; wherein said apparatus is capable of being implanted in a human or animal body and of providing long term treatment by blocking said activity of said area of a tissue and said circuitry is capable of delivering said therapy by controlling the magnitude and timing of said long non-excitatory electric pulses such that they are unable to generate a propagating action potential.

2. Apparatus as claimed in claim 1, comprising circuitry for controlling the start time of the electric potential generated between said at least two points.

3. Apparatus as claimed in claim 1, comprising circuitry for controlling the duration of the electric potential generated between said at least two points.

4. Apparatus as claimed in claim 2 or 3, wherein the circuitry for controlling the start time and/or duration of the electric potential is synchronized to heart activity.

5. Apparatus as claimed in claim 4, wherein the circuitry for controlling the start time and/or duration of the electric potential operates not at every beat of the heart.

6. Apparatus as claimed in claim 5, wherein the circuitry for controlling the start time and/or duration of the electric potential operates every 2 or 3 beats of the heart.

7. Apparatus as claimed in claim 1, comprising circuitry for controlling the magnitude of the electric potential generated between said at least two points.

8. Apparatus as claimed in claim 1, wherein at least some of the one or more electrodes are carbon electrodes.

9. Apparatus as claimed in claim 1, wherein the non-excitatory electric signal is a DC electric signal.

10. Apparatus for blocking the electric activity of an area of a tissue, said apparatus comprising one or more electrodes capable of being located in the vicinity of said area of a tissue and circuitry for creating long non-excitatory electric pulses and applying said pulses to said electrodes, thereby causing a long non-excitatory current to flow between at least two points located in the vicinity of said area of a tissue; wherein said apparatus is capable of being implanted in a human or animal body and of providing long term treatment by therapeutically blocking said activity of said area of a tissue and said circuitry is capable of delivering said therapy by controlling the magnitude and timing of said long non-excitatory electric current such that it is unable to generate a propagating action potential.

11. Apparatus for performing heart surgery, said apparatus comprising: one or more electrodes located in the vicinity of said area of a tissue; one or more sensors for sensing an activity of said area of a tissue; and circuitry for creating long non-excitatory electric pulses and applying said pulses to said electrodes, thereby generating a long non-excitatory potential between at least two points located in the vicinity of said area of a tissue; wherein said circuitry controls the magnitude and timing of said long non-excitatory electric pulses, in response to said activity sensed by said sensors, such that said long non-excitatory electric pulses are unable to generate a propagating action potential.

12. Apparatus as claimed in claim 11, comprising circuitry for controlling the start time of the electric potential generated between said at least two points.

13. Apparatus as claimed in claim 12, wherein the circuitry for controlling the start time of the electric potential is synchronized to heart activity.

14. Apparatus as claimed in claim 11, comprising circuitry for controlling the duration of the electric potential generated between said at least two points.

15. Apparatus as claimed in claim 14, wherein the circuitry for controlling the duration of the electric potential is synchronized to heart activity.

16. Apparatus as claimed in claim 13 or, wherein the circuitry for controlling the start time and/or duration of the electric potential operates not at every beat of the heart.

17. Apparatus as claimed in claim 16, wherein the circuitry for controlling the start time and/or duration of the electric potential operates every 2 or 3 beats of the heart.

18. Apparatus as claimed in claim 11, comprising circuitry for controlling the magnitude of the electric potential generated between said at least two points.

19. Apparatus as claimed in claim 11, wherein the electrodes are carbon electrodes.

20. Apparatus for performing heart surgery, said apparatus comprising one or more electrodes capable of being located in the vicinity of said area of a tissue; one or more sensors for sensing an activity of said area of a tissue; and circuitry for creating long non-excitatory electric pulses and applying said pulses to said electrodes, thereby causing a long non-excitatory current to flow in the vicinity of said area of a tissue; wherein said circuitry controls the magnitude and timing of said long non-excitatory electric pulses, in response to said activity sensed by said sensors, such that said long non-excitatory electric pulses are unable to generate a propagating action potential.

21. Apparatus as claimed in claim 20, comprising circuitry for controlling the start time of the electric current flowing between said at least two points.

22. Apparatus as claimed in claim 21, wherein the circuitry for controlling the start time of the electric current is synchronized to heart activity.

23. Apparatus as claimed in claim 20, comprising circuitry for controlling the duration of the electric current flowing between said at least two points.

24. Apparatus as claimed in claim 23, wherein the circuitry for controlling the duration of the electric current is synchronized to heart activity.

25. Apparatus as claimed in claim 24, wherein the circuitry for controlling the start time and/or duration of the electric current operates not at every beat of the heart.

26. Apparatus as claimed in claim 25, wherein the circuitry for controlling the start time and/or duration of the electric current operates every 2 or 3 beats of the heart.

27. Apparatus as claimed in claim 20, comprising circuitry for controlling the magnitude of the electric current flowing between said at least two points.

28. Apparatus as claimed in claim 20, wherein the electrodes are carbon electrodes.

29. Apparatus as claimed in claim 11 or 20, wherein the non-excitatory electric signal is a DC electric signal.

30. Apparatus for blocking the electric activity of an area of a tissue, comprising:
   circuitry for creating an electric potential of a magnitude and at a timing at which it is unable to generate a propagating action potential between at least two points located in the vicinity of said area of the tissue;
   circuitry for causing a non-excitatory electric current to flow between said at least two points thereby to generate a long non-excitatory electric signal; and
   circuitry for controlling the start time, duration and magnitude of the electric current flowing between said at least two points, such that the total duration of the long non-excitatory electric signal exceeds the threshold value at which the electric activity of the tissue is blocked,
   wherein said apparatus is capable of being implanted in a human or animal body and of providing long term treatment by blocking said electrical activity.

31. Apparatus for blocking the muscle activity of a cardiac muscle, comprising:
   circuitry for creating an electric potential of a magnitude and at a timing at which it is unable to generate a propagating action potential between at least two points located in the vicinity of the cardiac muscle;
   circuitry for causing a non-excitatory electric current to flow between said at least two points thereby to generate a long non-excitatory electric signal; and
   circuitry for controlling the start time, duration and magnitude of the electric current flowing between said at least two points, such that the total duration of the long non-excitatory electric signal exceeds half the duration of a contraction of the muscle, wherein said apparatus is capable of being implanted in a human or animal body and of providing long term treatment by blocking said muscle activity.

32. A method for providing long-term therapy by blocking the electric activity of an area of a tissue, said method comprising creating a long non-excitatory electric potential of a magnitude and at a timing at which it is unable to generate a propagating action potential between at least two points located in the vicinity of the tissue, and controlling one or more of the parameters consisting of start time, duration, magnitude and polarity of the long non-excitatory electric potential created between said at least two points.

33. A method for providing long-term therapy by blocking the electric activity of an area of a tissue, said method comprising causing a long non-excitatory electric current to flow in the vicinity of the tissue, and controlling one or more of the parameters consisting of start time, duration, magnitude and polarity of the long non-excitatory electric current such that said long non-excitatory electric current is unable to generate a propagating action potential between at least two points in the vicinity of said tissue.

34. A method for providing long-term therapy by blocking the electric activity of an area of a tissue, said method comprising the steps:
   (a) providing circuitry for creating an electric potential of a magnitude and at a timing at which it is unable to generate a propagating action potential between at least two points located in the vicinity of said area of the tissue;
   (b) providing circuitry for causing a non-excitatory electric current to flow between said at least two points; and
   (c) controlling the start time, duration and magnitude of the electric current flowing between said at least two points, such that the total duration of the long non-excitatory electric signal exceeds the threshold value at which the electric activity of the tissue is blocked.

35. A method of providing long-term therapy by treating a condition induced by electric activity of cells, said method comprising treating a patient in need thereof with the application of a long non-excitatory signal of a magnitude and at a timing at which it is unable to generate a propagating action potential consisting of an electric current flowing between at least two points located in the vicinity of the affected cells, such that the total duration of the long non-excitatory electric signal exceeds the threshold value at which the electric activity of the tissue is blocked.

36. Apparatus for blocking the activity of an area of a tissue, said apparatus comprising: one or more electrodes located in the vicinity of said area of a tissue; one or more sensors for sensing an activity of said area of a tissue; and circuitry for creating long non-excitatory electric pulses and applying said pulses to said electrodes, thereby generating a long non-excitatory potential between at least two points located in the vicinity of said area of a tissue; wherein said apparatus blocks said activity of said area of a tissue by using said circuitry to control the magnitude and timing of said long non-excitatory electric pulses, in response to said activity sensed by said sensors, such that said long non-excitatory electric pulses are unable to generate a propagating action potential.

37. Apparatus as claimed in claim 36, comprising circuitry for controlling the start time of the electric potential generated between said at least two points.

38. Apparatus as claimed in claim 36, comprising circuitry for controlling the duration of the electric potential generated between said at least two points.

39. Apparatus as claimed in claim 37 or 38, wherein the circuitry for controlling the start time and/or duration of the electric potential is synchronized to heart activity.

40. Apparatus as claimed in claim 39, wherein the circuitry for controlling the start time and/or duration of the electric potential operates not at every beat of the heart.

41. Apparatus as claimed in claim 40, wherein the circuitry for controlling the start time and/or duration of the electric potential operates every 2 or 3 beats of the heart.

42. Apparatus as claimed in claim 36, comprising circuitry for controlling the magnitude of the electric potential generated between said at least two points.

43. Apparatus as claimed in claim 36, wherein at least some of the one or more electrodes are carbon electrodes.

44. Apparatus for blocking the electric activity of an area of a tissue, said apparatus comprising: one or more electrodes located in the vicinity of said area of a tissue; one or more sensors for sensing an activity of said area of a tissue; and circuitry for creating long non-excitatory electric pulses and applying said pulses to said electrodes, thereby causing a long non-excitatory current to flow in the vicinity of said area of a tissue; wherein said apparatus blocks said activity of said area of a tissue by using said circuitry to control the magnitude and timing of said long non-excitatory electric pulses, in response to said activity sensed by said sensors, such that said long non-excitatory electric pulses are unable to generate a propagating action potential.

45. Apparatus as claimed in claim 10 or 44, comprising circuitry for controlling the start time of the electric current flowing between said at least two points.

46. Apparatus as claimed in claim 45, wherein the circuitry for controlling the start time and/or duration of the electric current is synchronized to heart activity.

47. Apparatus as claimed in claim 46, wherein the circuitry for controlling the start time and/or duration of the electric current operates not at every beat of the heart.

48. Apparatus as claimed in claim 47, wherein the circuitry for controlling the start time and/or duration of the electric current operates every 2 or 3 beats of the heart.

49. Apparatus as claimed in claim 10 or 44, comprising circuitry for controlling the duration of the electric current flowing between said at least two points.

50. Apparatus as claimed in claim 49, wherein the circuitry for controlling the start time and/or duration of the electric current is synchronized to heart activity.

51. Apparatus as claimed in claim 10 or 44, comprising circuitry for controlling the magnitude of the electric current flowing between said at least two points.

52. Apparatus as claimed in claim 10 or 44, wherein at least some of the one or more electrodes are carbon electrodes.

53. Apparatus for blocking the electric activity of an area of a tissue, comprising:
   circuitry for creating an electric potential of a magnitude and at a timing at which it is unable to generate a propagating action potential between at least two points located in the vicinity of said area of the tissue;
   circuitry for causing a non-excitatory electric current to flow between said at least two points thereby to generate a long non-excitatory electric signal;
   one or more sensors for sensing an activity of said area of a tissue; and
   circuitry for controlling the start time, duration and magnitude of the electric current flowing between said at least two points, such that the total duration of the long non-excitatory electric signal exceeds the threshold value at which the electric activity of the tissue is blocked, wherein said circuitry for controlling the start time, duration and magnitude of the electric current controls the start time, duration and magnitude of the electric current in response to said activity sensed by said sensors.

54. Apparatus for blocking the muscle activity of a cardiac muscle, comprising:

circuitry for creating an electric potential of a magnitude and at a timing at which it is unable to generate a propagating action potential between at least two points located in the vicinity of the cardiac muscle;

circuitry for causing a non-excitatory electric current to flow between said at least two points thereby to generate a long non-excitatory electric signal;

one or more sensors for sensing an activity of said cardiac muscle; and circuitry for controlling the start time, duration and magnitude of the electric current flowing between said at least two points, such that the total duration of the long non-excitatory electric signal exceeds half the duration of a contraction of the muscle, wherein said circuitry for controlling the start time, duration and magnitude of the electric current controls the start time, duration and magnitude of the electric current in response to said activity sensed by said sensors.

55. Apparatus according to claim 30, 31, 53, or 54, wherein the means for controlling the start time, duration and magnitude of the electric current flowing between said at least two points located in the vicinity of an area of the tissue comprise pulse generating means for generating a plurality of pulses, with a given frequency, and wherein the timing of said pulses is adapted to the activity of the tissue, the total duration of said series of pulses constituting the duration of the long non-excitatory signal.

56. Apparatus according to claim 30, 31, 53, or 54, further comprising means for superimposing on the DC signal one or more waveforms of given frequency and amplitude, to thereby generate a complex signal.

57. A method for blocking the electric activity of an area of a tissue, said method comprising: supplying one or more sensors for sensing an activity of said area of a tissue, creating a long non-excitatory electric potential of a magnitude and at a timing at which it is unable to generate a propagating action potential between at least two points located in the vicinity of the tissue, and controlling, in response to said activity sensed by said sensors, one or more of the parameters consisting of start time, duration, magnitude and polarity of the long non-excitatory electric potential created between said at least two points.

58. A method according to claim 33 or 57, wherein the non-excitatory electric current is a DC current.

59. A method according to claim 33 or 57, wherein the flow of the non-excitatory DC electric current is synchronized to heart activity.

60. A method according to claim 59, wherein the non-excitatory DC electric current flows not at every beat of the heart.

61. A method according to claim 60, wherein the non-excitatory DC electric current flows every 2 or 3 beats of the heart.

62. A method for blocking the electric activity of an area of a tissue, said method comprising: supplying one or more sensors for sensing an activity of said area of a tissue, causing a long non-excitatory electric current to flow in the vicinity of the tissue, and controlling, in response to said activity sensed by said sensors, one or more of the parameters consisting of start time, duration, magnitude and polarity of the long non-excitatory electric current such that said long non-excitatory electric current is unable to generate a propagating action potential between at least two points in the vicinity of said tissue.

63. A method according to claim 32, 33, 57, or 62, wherein the tissue is a muscle.

64. A method according to claim 63, wherein the muscle is a cardiac muscle.

65. A method for blocking the electric activity of an area of a tissue, said method comprising the steps:

(a) providing means for creating an electric potential of a magnitude and at a timing at which it is unable to generate a propagating action potential between at least two points located in the vicinity of said area of the tissue;

(b) providing means for causing a non-excitatory electric current to flow between said at least two points;

(c) supplying one or more sensors for sensing an activity of said area of a tissue; and (d) controlling, in response to said activity sensed by said sensors, the start time, duration and magnitude of the electric current flowing between said at least two points, such that the total duration of the long non-excitatory electric signal exceeds the threshold value at which the electric activity of the tissue is blocked.

66. A method of treating a condition induced by electric activity of cells, said method comprising supplying one or more sensors for sensing an activity of said cells and treating a patient in need thereof with the application, in response to said activity sensed by said sensors, of a long non-excitatory signal of a magnitude and at a timing at which it is unable to generate a propagating action potential said long non-excitatory signal consisting of an electric current flowing between at least two points located in the vicinity of the affected cells, such that the total duration of the long non-excitatory electric signal exceeds the threshold value at which the electric activity of the tissue is blocked.

* * * * *